(12) United States Patent
Cheng et al.

(10) Patent No.: US 6,428,996 B1
(45) Date of Patent: Aug. 6, 2002

(54) CELLULASE ENZYMES

(75) Inventors: Kuo-Joan Cheng, Richmond; Jin-Hao Liu, Calgary, both of (CA); Cheng-Fang Tsai, Taipei, Hsien; Yih-Chih Hsu, Taipei, both of (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 09/428,034

(22) Filed: Oct. 27, 1999

(51) Int. Cl.[7] .............................. C12N 9/42; C12N 1/20; C12N 15/00; C12N 5/00; C07H 21/04

(52) U.S. Cl. .................... 435/209; 435/200; 435/252.3; 435/320.1; 435/410; 536/23.2

(58) Field of Search ............................ 435/252.3, 320.1, 435/209, 200, 410; 536/23.2

(56) References Cited

U.S. PATENT DOCUMENTS

| | | | |
|---|---|---|---|
| 4,894,338 A | 1/1990 | Knowles et al. | 435/172.3 |
| 5,047,332 A | 9/1991 | Chahal | 435/42 |
| 5,120,463 A | 6/1992 | Bjork et al. | 252/174.12 |
| 5,432,074 A | 7/1995 | Evans et al. | 435/200 |
| 5,688,290 A | 11/1997 | Bjork et al. | 8/401 |
| 5,700,686 A | 12/1997 | Foody et al. | 435/263 |
| 6,222,028 B1 * | 4/2001 | Liu et al. | 536/23.2 |

OTHER PUBLICATIONS

Denman et al. Appl. Environ. Microbiol. 62 : 1889–1896 (1996).*

* cited by examiner

*Primary Examiner*—Tekchand Saidha
(74) *Attorney, Agent, or Firm*—Fish & Richardson P.C.

(57) ABSTRACT

The invention relates to a new cellulase enzyme isolated from the fungus *Piromyces rhizinflata* and nucleic acids encoding it.

8 Claims, No Drawings

CELLULASE ENZYMES

BACKGROUND OF THE INVENTION

Cellulases are enzymes that can hydrolyze the glycosidic linkages in polysaccharides such as cellulose. These enzymes are used in a number of industrial applications where breaking down biomass is beneficial. For example, cellulases can be used as a supplement in animal feed to decrease the production of fecal waste by increasing the digestibility of the feed. Cellulases can also be used to increase the efficiency of alcoholic fermentations (e.g., in beer brewing) by converting undigestible biomass into fermentable sugars. In addition, the "softening" of blue jeans to produce a "stone-washed" look can be facilitated by treating the jeans with cellulases.

SUMMARY OF THE INVENTION

The invention is based on the discovery of a new cellulase isolated from the fungus *Piromyces rhizinflata*. The gene encoding this cellulase is designated cbhA. A portion of an cbhA cDNA is described below.

Accordingly, the invention features a substantially pure polypeptide having an amino acid sequence at least 70% (e.g., at least 80, 90, or 95%) conserved with or identical to an amino acid sequence representing the catalytic domain of CBHA (SEQ ID NO:4; described below), the polypeptide encoded by cbhA. The polypeptide is capable of hydrolyzing a polysaccharide such as oat spelt xylan. Such a polysaccharide can also be cellulose (e.g., carboxymethyl cellulose), polysaccharides containing $\beta$-1,3' or $\beta$-1,4' glycosidic linkage (e.g., barley $\beta$-glycan), or lechinan.

The invention also includes an isolated nucleic acid encoding a polypeptide of the invention. For example, the invention includes an isolated nucleic acid having a sequence encoding a polypeptide that hydrolyzes a polysaccharide, provided that the nucleic acid hybridizes under stringent conditions to SEQ ID NO:1.

In addition, the invention features any vectors or transformed cells which contain a nucleic acid of the invention. Vectors include nucleic acid vectors, such as expression plasmids, or viral vectors. Transformed cells include eukaryotic and prokaryotic cells.

A "nucleic acid" encompasses both RNA and DNA, including cDNA, genomic DNA, and synthetic (e.g., chemically synthesized or modified) DNA. The nucleic acid may be double-stranded or single-stranded. Where single stranded, the nucleic acid may be a sense strand or an antisense strand. An "isolated nucleic acid" refers to a nucleic acid which may be flanked by non-natural sequences, such as those of a plasmid or virus. Thus, the nucleic acid can include none, some, or all of the 5' non-coding (e.g., promoter) sequences which are immediately contiguous to the coding sequence. The term, therefore, includes, for example, a recombinant DNA which is incorporated into a vector including an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other sequences. The term also includes a recombinant DNA or RNA which is part of a hybrid gene encoding an additional polypeptide sequence. Moreover, the term is meant to include nucleic acid fragments which are not naturally occurring as fragments and would not be found in the natural state.

By "hybridizes under stringent conditions" is meant specific and non-covalent binding to an immobilized reference nucleic acids in the presence of 0.2×SSC (1.75 g/l NaCl, 0.88 g/l Na$_3$citrate.2H$_2$O; pH 7.0) and 0.1% (w/v) sodium dodecylsulfate at 68° C.

The term "substantially pure" as used herein in reference to a given polypeptide means that the polypeptide is substantially free from other compounds, such as those in cellular material, viral material, or culture medium, with which the polypeptide may have been associated (e.g., in the course of production by recombinant DNA techniques or before purification from a natural biological source). The polypeptide is at least 75% (e.g., at least 80, 85, 95, or 99%) by weight pure. Purity can be measured by any appropriate standard method, for example, by column chromatography, polyacrylamide gel electrophoresis, or HPLC analysis.

Where a particular polypeptide or nucleic acid molecule is said to have a specific percent identity or conservation to a reference polypeptide or nucleic acid, the percent identity or conservation is determined by the algorithm of Myers and Miller, CABIOS (1989), which is embodied in the ALIGN program (version 2.0), or its equivalent, using a gap length penalty of 12 and a gap penalty of 4 where such parameters are required. All other parameters are set to their default positions. Access to ALIGN is readily available. See, e.g., http://www2.igh.cnrs.fr\/bin/align-guess.cgi on the Internet.

Other features or advantages of the present invention will be apparent from the following detailed description, the drawings, and also from the claims.

DETAILED DESCRIPTION OF THE INVENTION

The invention relates to a cellulase enzyme, nucleic acids encoding it, and vectors and cells containing such nucleic acids. Contemplated within the scope of this invention are recombinant nucleic acids or viruses which allow production of CBHA in a transformed cell or transgenic organism or allow ease of producing specific or non-specific mutations within the CBHA reading frame. These recombinant nucleic acids or viruses may further include any one of a variety of sequences flanking or within the CBHA coding sequences, such as strong constitutive promoters within the CBHA coding sequence, as introns containing cis-elements that allow high level expression, or efficient polyadenylation signals.

Without further elaboration, it is believed that one skilled in the art can, based on the above disclosure and the isolation of CBHA polypeptides and nucleic acids described below, utilize the present invention to its fullest extent. The following examples are to be construed as merely illustrative of how one skilled in the art can isolate and use CBHA polypeptides and nucleic acids from biological sources, and are not limitative of the remainder of the disclosure in any way. For example, once the sequence of the cbhA cDNA is known, any cbhA sequence can be obtained by PCR amplification of mRNA or genomic DNA. Any publications cited in this disclosure are hereby incorporated by reference.

The anaerobic fungus *Piromyces rhizinflata*, strain 2301, was cultivated anaerobically at 39° C. in a modified semi-defined medium as described in Lowe et al., J. Gen. Microbiol. 131:2225-2229, 1985. The mycelia were harvested from the culture media, lyophilized, frozen in liquid nitrogen, and ground into a powder. The powder was homogenized in extraction buffer containing 100 mM Tris-HCl (pH 8.0), 50 mM EDTA, 500 mM NaCl, 2% SDS, and 1% $\beta$-mercaptoethanol. An equal volume of a 1:1 mixture of phenol/chloroform was added, and the resulting mixture vortexed for 60 seconds and then centrifuged. The aqueous phase was extracted with the phenol/chloroform again. A one-third volume of 8 M LiCl was then added to the extracted mixture. The mixture was centrifuged sufficiently to pellet the RNA, which was washed with 2 M LiCl, followed by 80% ethanol. The washed RNA was then resuspended in diethyl pyrocarbonate (DEPC)-treated water.

Polyadenylated RNA was isolated from total RNA using a standard oligo-(dT)-cellulose chromatography column. The construction of a cDNA expression library was carried out using a Stratagene kit. The library was screened for cellulase activity by overlaying plaques with 0.7% (w/v) agarose containing 0.2% (w/v) carboxymethyl cellulose (CMC). The plates were incubated at 39° C. overnight, then stained with a 0.1% (w/v) aqueous solution of Congo red and destained with 1 M NaCl as described in Teather et al., App. Environ. Microbiol. 43:777-780, 1982. Cellulase-producing plaques were surrounded by a clear halo visible against a red background. The positive clones were excised and purified using standard procedures. One of the clones, designated pPr2301-16, was selected for further study. The mRNA and gene from which the cDNA residing in pPr2301-16 was designated cbhA.

The complete sequence of the cDNA insert in plasmid pPr2301-16 was determined using a commercial service (Bio S&T, Lachine, QC, Canada). Translation of one reading frame revealed a 1128 bp open reading frame, as shown below.

```
   1 GAA ACT CTT CCA CAA CAA TCT AAC TCC GCA AAA ACG CTT CCA CAA CAA TCT GAC TCT GCA    60
   1 E   T   L   P   Q   Q   S   N   S   A   K   T   L   P   Q   Q   S   D   S   A     20

61 AAA ACA ATT CCA CAA CCC ACT TCA GCA GAA TCA CAA ACT TCA AAG ACA CTT CCA CAA ACA   120
  21 K   T   I   P   Q   P   T   S   A   E   S   Q   T   S   K   T   L   P   Q   T    40

121 GGA GGC AGT GGT AAT GGT AGT AGT CAA AAC TTT TTC TTA AAT GAA ATT TAT GCT AAT CCA   180
  41 G   G   S   G   N   G   S   S   Q   N   F   F   L   N   E   I   Y   A   N   P    60

181 AAA TTC ATT GAA GAA GTT GAA GAT TCC ATT GAA AAA TTA ACT CCT GAA TTA CAA GCT AAG   240
  61 K   F   I   E   E   V   E   D   S   I   E   K   L   T   P   E   L   Q   A   K    80

241 GCC GAA AAG GTC AAG GAT GTT CCA ACT GCT GTT TGG TTA GCT TGG GAT GGT TCT CCA GGT   300
  81 A   E   K   V   K   D   V   P   T   A   V   W   L   A   W   D   G   S   P   G   100

301 GAA GTT GAA GGT CAT CTT GTT GCT GCC GGT TCT AAG ACT GTT GTA TTC CTT CTT TAC ATG   360
 101 E   V   E   G   M   L   V   A   A   G   S   K   T   V   V   F   L   L   Y   M   120

361 ATT CCA ACT CGT GAT TGT AAC AGT AAT GCT TCT GCT GGT GGT GCT GCT AGT CTT GAT AAA   420
 121 I   P   T   R   D   C   N   S   N   A   S   A   G   G   A   A   S   L   D   K   140

421 TAT AAG GGT TAT ATC GAT GAC ATT TCA AAC ACT ATC AAG AGT CAT CCA GAA TCA AAG GTT   480
 141 Y   K   G   Y   I   D   D   I   S   N   T   I   K   S   M   P   E   S   K   V   160

481 GTT ATG GTT GTT GAA CCA GAT ACT CTC GGT AAT CTC GTT ACT GGT AAT AGT GAA GCA TGT   540
 161 V   M   V   V   E   R   D   T   L   G   N   L   V   T   G   N   S   E   A   C   180

541 AAA AAT GTT CAC ACT TTA CAC AAG AAT GCC TTA TCT TAC GCT GTT GAT GTC TTT GGT GCT   600
 181 K   N   V   H   T   L   H   K   N   A   L   S   Y   A   V   D   V   F   G   A   200

601 ATG AGC AAT GTT AGT GTT TAT CTT GAT GCA GCT CAT GGT ATG TGG TTA GGT CCT CAC ACT   660
 201 M   S   N   V   S   V   Y   L   D   A   A   H   G   M   W   L   G   P   H   T   220

661 GAT AAG GTT GCT TCT GTC ATT AAA GAA ATT TTA AAT AAT GCT CCA AAT GGT AAG ATT CGT   720
 221 D   K   V   A   S   V   I   K   E   I   L   N   N   A   P   N   G   K   Z   R   240

721 GGT TTA AGT ACC AAT GTG TCA AAC TAC CAA CCA GTC AGT TCT GAA TAC CAA TAC CAT CAA   780
 241 G   L   S   T   N   V   S   N   Y   Q   P   V   S   S   E   Y   Q   Y   H   Q   260

781 AAA CTC GCT GCT TCT CTT GCC GCC GTT GGT GTT AAT GAC GTT CAT TTC ATT GTC GAT ACT   840
 261 K   L   A   A   S   L   A   A   V   G   V   N   D   V   H   F   I   V   D   T   280

841 GGT CGT AGT GGT GTT GAT GTT ACT GAA ACT TTC AGT AAA CAA CAA ACT TGG TGT AAC TTT   900
 281 G   R   S   G   V   D   V   T   E   T   F   S   K   Q   Q   T   W   C   N   F   300

901 ATT GGT GCT GGT TTA GGT CCA CGT CCA CAA GGT AAC CCA GAT GCT AGT ATG CCA TTA TTA   960
 301 I   G   A   G   L   G   P   R   P   Q   G   N   P   D   A   S   M   P   L   L   320

961 GAT GCC TAC ATG TGG CTC AAG ACT CCA GGG GAA GCT GAT GGA TCT GCT GTT GGT GAC AGA  1020
 321 D   A   Y   M   W   L   K   T   P   G   E   A   D   G   S   A   V   G   D   R   340

1021 GCT GAT CCA GTT TGT TCT CAT GAA GAT TCT CTT CAA GTT GCA CCA GAT GCA GGT CAA TGG  1080
 341 A   D   P   V   C   S   H   E   D   S   L   Q   V   A   P   D   A   G   Q   W   360

1081 TTC CAC GAT TAC TTC GTC CTC TTA TTA AAA AAT GCT AAT CCA CCA TTC TAA ataaattaaaaa 1143
 361 F   H   D   Y   F   V   L   L   K   N   A   N   P   P   F   *                   377
```

-continued

```
1144 aaaaaaaattattttttacatataatataaaaatataattatttttatttttttttttcatttactattaattaataataat  1223

1224 taataataataacaAaaaatatttaaattatatttttattaatgtaataatttatatttatttctattctttgttgtatta  1303

1304 ttatttaatcatcaatgaatgattatcttatataaataaaaattataaacatataaattat                      1364
```

This partial cDNA sequence (SEQ ID NO:1) of an cbhA from *Piromyces rhizinflata* encodes the partial CBHA amino acid sequence (SEQ ID NO:2) shown immediately above. No translation initiation codon was found at the 5' end, suggesting that the cDNA is incomplete.

Using previously known cellulase genes as a model, the cDNA of the pPr2301-16 clone appeared to be missing a N-terminal catalytic domain but includes a complete C-terminal catalytic domain. Based on this assumption, amino acids 44-376 of the above polypeptide sequence was considered to be a catalytic domain of CBHA and was further characterized.

The nucleic acid sequence encoding the putative CBHA catalytic domain was amplified by PCR using primers 16F (GCA<u>GGATCC</u>GGTAATGGTAGTAGTCAAA; SEQ ID NO:5) and 16R (GTAG<u>CTCGAG</u>TAGAATGGTGGATTAGC; SEQ ID NO:6). To facilitate cloning, 16F contains a BamHI site, while 16R contains a XhoI site; both restriction sites are underlined in the primer sequences immediately above. The PCR product was then digested with the appropriate enzymes and ligated into BamHI and XhoI digested pGEX-4T-3 (Pharmacia Biotech, Inc.) to produce the Glutathione S-transferase (GST)-fusion expression plasmid PGEX-CBHA. The CBHA amino acid sequence downstream of the GST is shown below. The underlined sequence at the 5' and 3' ends indicates the binding site for primers 16F and 16R.

```
  1 GGT AAT GGT AGT AGT CAA AAC TTT TTC TTA AAT GAA ATT TAT GCT AAT CCA AAA TTC ATT   60
  1 G   N   G   S   S   Q   N   F   F   L   N   E   I   Y   A   N   P   K   F   I    20

61 GAA GAA GTT GAA GAT TCC ATT GAA AAA TTA ACT CCT GAA TTA CAA GCT AAG GCC GAA AAG  120
 21 E   E   V   E   D   S   I   E   K   L   T   P   E   L   Q   A   K   A   E   K    40

121 GTC AAG GAT GTT CCA ACT GCT GTT TGG TTA GCT TGG GAT GGT TCT CCA GGT CAA GTT GAA  180
 41 V   K   D   V   P   T   A   V   W   L   A   W   D   G   S   P   G   Q   V   E    60

181 GGT CAT CTT GTT GCT GCC GGT TCT AAG ACT GTT GTA TTC CTT CTT TAC ATG ATT CCA ACT  240
 61 G   H   L   V   A   A   G   S   K   T   V   V   F   L   L   Y   H   I   P   T    80

241 CGT GAT TGT AAC AGT AAT GCT TCT GCT GGT GGT GCT GCT AGT CTT GAT AAA TAT AAG GGT  300
 81 R   D   C   N   S   N   A   S   A   G   G   A   A   S   L   D   K   Y   K   G   100

301 TAT ATC GAT GAC ATT TCA AAC ACT ATC AAG AGT CAT CCA GAA TCA AAG GTT GTT ATG GTT  360
101 Y   I   D   D   I   S   N   T   I   K   S   H   P   E   S   K   V   V   M   V   120

361 GTT GAA CCA GAT ACT CTC GGT AAT CTC GTT ACT GGT AAT AGT GAA GCA TGT AAA AAT GTT  420
121 V   E   P   D   T   L   G   N   L   V   T   G   N   S   E   A   C   K   N   V   140

421 CAC ACT TTA GAC AAG AAT GCC TTA TCT TAC GCT GTT GAT GTC TTT GGT GCT ATG AGC AAT  480
141 H   T   L   H   K   N   A   L   S   Y   A   V   D   V   F   G   A   M   S   N   160

481 GTT AGT GTT TAT CTT GAT GCA GCT CAT GGT ATG TGG TTA GGT CCT CAC ACT GAT AAG GTT  540
161 V   S   V   Y   L   D   A   A   H   G   M   W   L   G   P   H   T   D   K   V   180

541 GCT TCT GTC ATT AAA GAA ATT TTA AAT AAT GCT CCA AAT GGT AAG ATT CGT GGT TTA AGT  600
181 A   S   V   I   K   E   I   L   N   N   A   P   N   G   K   I   R   G   L   S   200

601 ACC AAT GTG TCA AAC TAC CAA CCA GTC AGT TCT GAA TAC CAA TAC CAT CAA AAA CTC GCT  660
201 T   N   V   S   N   Y   Q   P   V   S   S   E   Y   Q   Y   H   Q   K   L   A   220

661 GCT TCT CTT GCC GCC GTT GGT GTT AAT GAC GTT CAT TTC ATT GTC GAT ACT GGT CGT AGT  720
221 A   S   L   A   A   V   G   V   N   D   V   H   F   I   V   D   T   G   R   S   240

721 GGT GTT GAT GTT ACT GAA ACT TTC AGT AAA CAA CAA ACT TGG TGT AAC TTT ATT GGT GCT  780
241 G   V   D   V   T   R   T   F   S   K   Q   Q   T   W   C   N   F   I   G   A   260

781 GGT TTA GGT CCA CGT CCA CAA GGT AAC CCA GAT GCT AGT ATG ATT ATT AGA TGC TAC ATG  840
261 G   L   G   P   R   P   Q   G   N   P   D   A   S   M   I   I   R   C   Y   M   280

841 TGG CTC AAG ACT CCA GGG GAA GCT GAT GGA TCT GCT GTT GGT GAC AGA GCT GAT CCA GTT  900
281 W   L   K   T   P   G   E   A   D   G   S   A   V   G   D   R   A   D   P   V   300

901 TGT TCT CAT GAA GAT TCT CTT CAA GTT GCA CCA GAT GCA GGT CAA TGG TTC CAC GAT TAC  960
301 C   S   H   E   D   S   L   Q   V   A   P   D   A   G   Q   W   F   H   D   Y   320

961 TTC GTC CTC TTA TTA AAA AAT GCT AAT CCA CCA TTC TAA
321 F   V   L   L   K   N   A   N   P   P   F   *                                    333
```

The complete nucleic acid sequence immediately above is designated SEQ ID NO:3, and the complete amino acid sequence encoded by that nucleic acid sequence is designated SEQ ID NO:4. SEQ ID NO:3 correspond to nucleotides 131-1131 of SEQ ID NO:1. SEQ ID NO:4 corresponds to amino acids 44-377 of SEQ ID NO:2.

The CBHA catalytic domain expression plasmid was used to transformed *E. coli* to produce recombinant CBHA. GST-CBHA was purified on glutathione Sepharose 4B (Pharmacia Biotech, Inc.) following the manufacturer's protocols. Bound fusion protein was cleaved with thrombin to release only the CBHA catalytic domain.

The enzymatic activity of the CBHA fragment was determined as follows. The purified protein was suspended in 50 mM sodium phosphate buffer containing 1% CMC, 1% oat spelt xylan, 0.4% barley β-glucan, 1% lechinan, 5 mM pNP-β-D-glucoside, Avicel, or 5 mM pNP-β-D-cellobioside. The barley βglucan contains mixed β-1,3'-1,4' glucan. Enzymatic activity was measured by detecting the amount of reducing sugar released from the substrate. After incubating the reaction at 37° C. for 15 minutes, the reaction was stopped by adding a half-volume each of 0.3% (w/v) 3,6-dinitrophthalic acid and stop solution (25% $K_2CO_3$ and 5% $Na_2S_2O_3$). The stopped reaction was then boiled for 10 minutes before the absorbance at 450 nm was read. Protein concentrations were measured using a protein assay kit (BioRad). The results are summarized in Table 1 below.

TABLE 1

| Substrate | Specific Activity (μmoles glucose/mg/min) | Relative Activity (%) |
| --- | --- | --- |
| Carboxymethyl cellulose | 233.2 | 100 |
| Barley β-glucan | 87.0 | 37 |
| Lechinan | 546.3 | 234 |
| Oat Spelt Xylan | 871.3 | 374 |

No activity was detected using pNP-β-D-glucoside, Avicel, or pNP-β-D-cellobioside as a substrate under these conditions.

Using the assay described immediately above, the temperature or pH was varied to obtain conditions necessary for optimal activity. The optimal temperature for the CBHA catalytic domain was about 40° C., and the optimal pH for the catalytic domain was about 6.5.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of this invention.

What is claimed is:

1. An isolated nucleic acid encoding a substantially pure polypeptide comprising an amino acid sequence at least 85% identical to SEQ ID NO:4, wherein the polypeptide hydrolyzes a polysaccharide containing a β-1,3' or β-1,4' glycosidic linkage.

2. The isolated nucleic acid of claim 1, wherein the amino acid sequence is at least 90% identical to SEQ ID NO:4.

3. The isolated nucleic acid of claim 2, wherein the amino acid sequence is at least 95% identical to SEQ ID NO:4.

4. The isolated nucleic acid of claim 3, wherein the amino acid sequence is SEQ ID NO:4.

5. The isolated nucleic acid of claim 1, wherein the polysaccharide is cellulose.

6. An isolated nucleic acid comprising a sequence encoding a polypeptide that hydrolyzes a polysaccharide containing a β-1,3' or β-1,4' glycosidic linkage, wherein the nucleic acid hybridizes under stringent conditions to SEQ ID NO:1.

7. A vector comprising the nucleic acid of claim 6.

8. A transformed cell comprising the nucleic acid of claim 6.

* * * * *

SEQUENCE LISTING

<160> NUMBER OF SEQ ID NOS: 6

<210> SEQ ID NO 1
<211> LENGTH: 1364
<212> TYPE: DNA
<213> ORGANISM: Piromyces rhizinflata
<220> FEATURE:
<221> NAME/KEY: CDS
<222> LOCATION: (1)...(1128)

<400> SEQUENCE: 1

```
gaa act ctt cca caa caa tct aac tcc gca aaa acg ctt cca caa caa      48
Glu Thr Leu Pro Gln Gln Ser Asn Ser Ala Lys Thr Leu Pro Gln Gln
 1               5                  10                  15 tct gac tct gca aaa aca att cca caa ccc act tca gca gaa tca caa      96
Ser Asp Ser Ala Lys Thr Ile Pro Gln Pro Thr Ser Ala Glu Ser Gln
                20                  25                  30 act tca aag aca ctt cca caa aca gga ggc agt ggt aat ggt agt agt     144
Thr Ser Lys Thr Leu Pro Gln Thr Gly Gly Ser Gly Asn Gly Ser Ser
            35                  40                  45 caa aac ttt ttc tta aat gaa att tat gct aat cca aaa ttc att gaa     192
Gln Asn Phe Phe Leu Asn Glu Ile Tyr Ala Asn Pro Lys Phe Ile Glu
        50                  55                  60 gaa gtt gaa gat tcc att gaa aaa tta act cct gaa tta caa gct aag     240
Glu Val Glu Asp Ser Ile Glu Lys Leu Thr Pro Glu Leu Gln Ala Lys
    65                  70                  75                  80 gcc gaa aag gtc aag gat gtt cca act gct gtt tgg tta gct tgg gat     288
Ala Glu Lys Val Lys Asp Val Pro Thr Ala Val Trp Leu Ala Trp Asp
                    85                  90                  95 ggt tct cca ggt gaa gtt gaa ggt cat ctt gtt gct gcc ggt tct aag     336
```

```
Gly Ser Pro Gly Glu Val Glu Gly His Leu Val Ala Ala Gly Ser Lys
         100                 105                 110 act gtt gta ttc ctt ctt tac atg att cca act cgt gat tgt aac agt      384
Thr Val Val Phe Leu Leu Tyr Met Ile Pro Thr Arg Asp Cys Asn Ser
        115                 120                 125 aat gct tct gct ggt ggt gct gct agt ctt gat aaa tat aag ggt tat      432
Asn Ala Ser Ala Gly Gly Ala Ala Ser Leu Asp Lys Tyr Lys Gly Tyr
    130                 135                 140 atc gat gac att tca aac act atc aag agt cat cca gaa tca aag gtt      480
Ile Asp Asp Ile Ser Asn Thr Ile Lys Ser His Pro Glu Ser Lys Val
145                 150                 155                 160 gtt atg gtt gtt gaa cca gat act ctc ggt aat ctc gtt act ggt aat      528
Val Met Val Val Glu Pro Asp Thr Leu Gly Asn Leu Val Thr Gly Asn
                165                 170                 175 agt gaa gca tgt aaa aat gtt cac act tta cac aag aat gcc tta tct      576
Ser Glu Ala Cys Lys Asn Val His Thr Leu His Lys Asn Ala Leu Ser
            180                 185                 190 tac gct gtt gat gtc ttt ggt gct atg agc aat gtt agt gtt tat ctt      624
Tyr Ala Val Asp Val Phe Gly Ala Met Ser Asn Val Ser Val Tyr Leu
        195                 200                 205 gat gca gct cat ggt atg tgg tta ggt cct cac act gat aag gtt gct      672
Asp Ala Ala His Gly Met Trp Leu Gly Pro His Thr Asp Lys Val Ala
    210                 215                 220 tct gtc att aaa gaa att tta aat aat gct cca aat ggt aag att cgt      720
Ser Val Ile Lys Glu Ile Leu Asn Asn Ala Pro Asn Gly Lys Ile Arg
225                 230                 235                 240 ggt tta agt acc aat gtg tca aac tac caa cca gtc agt tct gaa tac      768
Gly Leu Ser Thr Asn Val Ser Asn Tyr Gln Pro Val Ser Ser Glu Tyr
                245                 250                 255 caa tac cat caa aaa ctc gct gct tct ctt gcc gcc gtt ggt gtt aat      816
Gln Tyr His Gln Lys Leu Ala Ala Ser Leu Ala Ala Val Gly Val Asn
            260                 265                 270 gac gtt cat ttc att gtc gat act ggt cgt agt ggt gtt gat gtt act      864
Asp Val His Phe Ile Val Asp Thr Gly Arg Ser Gly Val Asp Val Thr
        275                 280                 285 gaa act ttc agt aaa caa caa act tgg tgt aac ttt att ggt gct ggt      912
Glu Thr Phe Ser Lys Gln Gln Thr Trp Cys Asn Phe Ile Gly Ala Gly
    290                 295                 300 tta ggt cca cgt cca caa ggt aac cca gat gct agt atg cca tta tta      960
Leu Gly Pro Arg Pro Gln Gly Asn Pro Asp Ala Ser Met Pro Leu Leu
305                 310                 315                 320 gat gcc tac atg tgg ctc aag act cca ggg gaa gct gat gga tct gct     1008
Asp Ala Tyr Met Trp Leu Lys Thr Pro Gly Glu Ala Asp Gly Ser Ala
                325                 330                 335 gtt ggt gac aga gct gat cca gtt tgt tct cat gaa gat tct ctt caa     1056
Val Gly Asp Arg Ala Asp Pro Val Cys Ser His Glu Asp Ser Leu Gln
            340                 345                 350 gtt gca cca gat gca ggt caa tgg ttc cac gat tac ttc gtc ctc tta     1104
Val Ala Pro Asp Ala Gly Gln Trp Phe His Asp Tyr Phe Val Leu Leu
        355                 360                 365 tta aaa aat gct aat cca cca ttc taaataaatt aaaaaaaaa aaattatttt     1158
Leu Lys Asn Ala Asn Pro Pro Phe
    370                 375 tacatataat ataaaatat aattatttt attttttttt tcatttacta ttaattaata     1218
ataattaata ataatacaaa aaatatttaa attatatttt tattaatgta ataatttata     1278
tttatttcta ttctttgttg tattattatt taatcatcaa tgaatgatta tcttatataa     1338
ataaaaatta taaacatata aattat                                          1364
```

```
<210> SEQ ID NO 2
<211> LENGTH: 376
<212> TYPE: PRT
<213> ORGANISM: Piromyces rhizinflata

<400> SEQUENCE: 2

Glu Thr Leu Pro Gln Gln Ser Asn Ser Ala Lys Thr Leu Pro Gln Gln
  1               5                  10                  15

Ser Asp Ser Ala Lys Thr Ile Pro Gln Pro Thr Ser Ala Glu Ser Gln
             20                  25                  30

Thr Ser Lys Thr Leu Pro Gln Thr Gly Gly Ser Gly Asn Gly Ser Ser
         35                  40                  45

Gln Asn Phe Phe Leu Asn Glu Ile Tyr Ala Asn Pro Lys Phe Ile Glu
     50                  55                  60

Glu Val Glu Asp Ser Ile Glu Lys Leu Thr Pro Glu Leu Gln Ala Lys
 65                  70                  75                  80

Ala Glu Lys Val Lys Asp Val Pro Thr Ala Val Trp Leu Ala Trp Asp
                 85                  90                  95

Gly Ser Pro Gly Glu Val Glu Gly His Leu Val Ala Ala Gly Ser Lys
            100                 105                 110

Thr Val Val Phe Leu Leu Tyr Met Ile Pro Thr Arg Asp Cys Asn Ser
        115                 120                 125

Asn Ala Ser Ala Gly Gly Ala Ala Ser Leu Asp Lys Tyr Lys Gly Tyr
    130                 135                 140

Ile Asp Asp Ile Ser Asn Thr Ile Lys Ser His Pro Glu Ser Lys Val
145                 150                 155                 160

Val Met Val Val Glu Pro Asp Thr Leu Gly Asn Leu Val Thr Gly Asn
                165                 170                 175

Ser Glu Ala Cys Lys Asn Val His Thr Leu His Lys Asn Ala Leu Ser
            180                 185                 190

Tyr Ala Val Asp Val Phe Gly Ala Met Ser Asn Val Ser Val Tyr Leu
        195                 200                 205

Asp Ala Ala His Gly Met Trp Leu Gly Pro His Thr Asp Lys Val Ala
    210                 215                 220

Ser Val Ile Lys Glu Ile Leu Asn Asn Ala Pro Asn Gly Lys Ile Arg
225                 230                 235                 240

Gly Leu Ser Thr Asn Val Ser Asn Tyr Gln Pro Val Ser Ser Glu Tyr
                245                 250                 255

Gln Tyr His Gln Lys Leu Ala Ala Ser Leu Ala Ala Val Gly Val Asn
            260                 265                 270

Asp Val His Phe Ile Val Asp Thr Gly Arg Ser Gly Val Asp Val Thr
        275                 280                 285

Glu Thr Phe Ser Lys Gln Gln Thr Trp Cys Asn Phe Ile Gly Ala Gly
    290                 295                 300

Leu Gly Pro Arg Pro Gln Gly Asn Pro Asp Ala Ser Met Pro Leu Leu
305                 310                 315                 320

Asp Ala Tyr Met Trp Leu Lys Thr Pro Gly Glu Ala Asp Gly Ser Ala
                325                 330                 335

Val Gly Asp Arg Ala Asp Pro Val Cys Ser His Glu Asp Ser Leu Gln
            340                 345                 350

Val Ala Pro Asp Ala Gly Gln Trp Phe His Asp Tyr Phe Val Leu Leu
        355                 360                 365

Leu Lys Asn Ala Asn Pro Pro Phe
    370                 375
```

<210> SEQ ID NO 3
<211> LENGTH: 999
<212> TYPE: DNA
<213> ORGANISM: Piromyces rhizinflata
<220> FEATURE:
<221> NAME/KEY: CDS
<222> LOCATION: (1)...(996)

<400> SEQUENCE: 3

```
ggt aat ggt agt agt caa aac ttt ttc tta aat gaa att tat gct aat      48
Gly Asn Gly Ser Ser Gln Asn Phe Phe Leu Asn Glu Ile Tyr Ala Asn
 1               5                  10                  15 cca aaa ttc att gaa gaa gtt gaa gat tcc att gaa aaa tta act cct      96
Pro Lys Phe Ile Glu Glu Val Glu Asp Ser Ile Glu Lys Leu Thr Pro
             20                  25                  30 gaa tta caa gct aag gcc gaa aag gtc aag gat gtt cca act gct gtt     144
Glu Leu Gln Ala Lys Ala Glu Lys Val Lys Asp Val Pro Thr Ala Val
         35                  40                  45 tgg tta gct tgg gat ggt tct cca ggt gaa gtt gaa ggt cat ctt gtt     192
Trp Leu Ala Trp Asp Gly Ser Pro Gly Glu Val Glu Gly His Leu Val
     50                  55                  60 gct gcc ggt tct aag act gtt gta ttc ctt ctt tac atg att cca act     240
Ala Ala Gly Ser Lys Thr Val Val Phe Leu Leu Tyr Met Ile Pro Thr
 65                  70                  75                  80 cgt gat tgt aac agt aat gct tct gct ggt ggt gct gct agt ctt gat     288
Arg Asp Cys Asn Ser Asn Ala Ser Ala Gly Gly Ala Ala Ser Leu Asp
                 85                  90                  95 aaa tat aag ggt tat atc gat gac att tca aac act atc aag agt cat     336
Lys Tyr Lys Gly Tyr Ile Asp Asp Ile Ser Asn Thr Ile Lys Ser His
            100                 105                 110 cca gaa tca aag gtt gtt atg gtt gtt gaa cca gat act ctc ggt aat     384
Pro Glu Ser Lys Val Val Met Val Val Glu Pro Asp Thr Leu Gly Asn
        115                 120                 125 ctc gtt act ggt aat agt gaa gca tgt aaa aat gtt cac act tta cac     432
Leu Val Thr Gly Asn Ser Glu Ala Cys Lys Asn Val His Thr Leu His
    130                 135                 140 aag aat gcc tta tct tac gct gtt gat gtc ttt ggt gct atg agc aat     480
Lys Asn Ala Leu Ser Tyr Ala Val Asp Val Phe Gly Ala Met Ser Asn
145                 150                 155                 160 gtt agt gtt tat ctt gat gca gct cat ggt atg tgg tta ggt cct cac     528
Val Ser Val Tyr Leu Asp Ala Ala His Gly Met Trp Leu Gly Pro His
                165                 170                 175 act gat aag gtt gct tct gtc att aaa gaa att tta aat aat gct cca     576
Thr Asp Lys Val Ala Ser Val Ile Lys Glu Ile Leu Asn Asn Ala Pro
            180                 185                 190 aat ggt aag att cgt ggt tta agt acc aat gtg tca aac tac caa cca     624
Asn Gly Lys Ile Arg Gly Leu Ser Thr Asn Val Ser Asn Tyr Gln Pro
        195                 200                 205 gtc agt tct gaa tac caa tac cat caa aaa ctc gct gct tct ctt gcc     672
Val Ser Ser Glu Tyr Gln Tyr His Gln Lys Leu Ala Ala Ser Leu Ala
    210                 215                 220 gcc gtt ggt gtt aat gac gtt cat ttc att gtc gat act ggt cgt agt     720
Ala Val Gly Val Asn Asp Val His Phe Ile Val Asp Thr Gly Arg Ser
225                 230                 235                 240 ggt gtt gat gtt act gaa act ttc agt aaa caa caa act tgg tgt aac     768
Gly Val Asp Val Thr Glu Thr Phe Ser Lys Gln Gln Thr Trp Cys Asn
                245                 250                 255 ttt att ggt gct ggt tta ggt cca cgt cca caa ggt aac cca gat gct     816
Phe Ile Gly Ala Gly Leu Gly Pro Arg Pro Gln Gly Asn Pro Asp Ala
            260                 265                 270
```

```
agt atg att att aga tgc tac atg tgg ctc aag act cca ggg gaa gct    864
Ser Met Ile Ile Arg Cys Tyr Met Trp Leu Lys Thr Pro Gly Glu Ala
        275                 280                 285 gat gga tct gct gtt ggt gac aga gct gat cca gtt tgt tct cat gaa    912
Asp Gly Ser Ala Val Gly Asp Arg Ala Asp Pro Val Cys Ser His Glu
    290                 295                 300 gat tct ctt caa gtt gca cca gat gca ggt caa tgg ttc cac gat tac    960
Asp Ser Leu Gln Val Ala Pro Asp Ala Gly Gln Trp Phe His Asp Tyr
305                 310                 315                 320 ttc gtc ctc tta tta aaa aat gct aat cca cca ttc taa                999
Phe Val Leu Leu Leu Lys Asn Ala Asn Pro Pro Phe
                325                 330
```

<210> SEQ ID NO 4
<211> LENGTH: 332
<212> TYPE: PRT
<213> ORGANISM: Piromyces rhizinflata

<400> SEQUENCE: 4

```
Gly Asn Gly Ser Ser Gln Asn Phe Phe Leu Asn Glu Ile Tyr Ala Asn
 1               5                  10                  15

Pro Lys Phe Ile Glu Glu Val Glu Asp Ser Ile Glu Lys Leu Thr Pro
             20                  25                  30

Glu Leu Gln Ala Lys Ala Glu Lys Val Lys Asp Val Pro Thr Ala Val
         35                  40                  45

Trp Leu Ala Trp Asp Gly Ser Pro Gly Glu Val Glu Gly His Leu Val
     50                  55                  60

Ala Ala Gly Ser Lys Thr Val Val Phe Leu Leu Tyr Met Ile Pro Thr
 65                  70                  75                  80

Arg Asp Cys Asn Ser Asn Ala Ser Ala Gly Gly Ala Ala Ser Leu Asp
                 85                  90                  95

Lys Tyr Lys Gly Tyr Ile Asp Asp Ser Asn Thr Ile Lys Ser His
             100                 105                 110

Pro Glu Ser Lys Val Val Met Val Val Glu Pro Asp Thr Leu Gly Asn
         115                 120                 125

Leu Val Thr Gly Asn Ser Glu Ala Cys Lys Asn Val His Thr Leu His
     130                 135                 140

Lys Asn Ala Leu Ser Tyr Ala Val Asp Val Phe Gly Ala Met Ser Asn
145                 150                 155                 160

Val Ser Val Tyr Leu Asp Ala Ala His Gly Met Trp Leu Gly Pro His
                 165                 170                 175

Thr Asp Lys Val Ala Ser Val Ile Lys Glu Ile Leu Asn Asn Ala Pro
             180                 185                 190

Asn Gly Lys Ile Arg Gly Leu Ser Thr Asn Val Ser Asn Tyr Gln Pro
         195                 200                 205

Val Ser Ser Glu Tyr Gln Tyr His Gln Lys Leu Ala Ala Ser Leu Ala
     210                 215                 220

Ala Val Gly Val Asn Asp Val His Phe Ile Val Asp Thr Gly Arg Ser
225                 230                 235                 240

Gly Val Asp Val Thr Glu Thr Phe Ser Lys Gln Gln Thr Trp Cys Asn
                 245                 250                 255

Phe Ile Gly Ala Gly Leu Gly Pro Arg Pro Gln Gly Asn Pro Asp Ala
             260                 265                 270

Ser Met Ile Ile Arg Cys Tyr Met Trp Leu Lys Thr Pro Gly Glu Ala
         275                 280                 285
```

-continued

```
Asp Gly Ser Ala Val Gly Asp Arg Ala Asp Pro Val Cys Ser His Glu
    290                 295                 300
Asp Ser Leu Gln Val Ala Pro Asp Ala Gly Gln Trp Phe His Asp Tyr
305                 310                 315                 320
Phe Val Leu Leu Leu Lys Asn Ala Asn Pro Pro Phe
                325                 330

<210> SEQ ID NO 5
<211> LENGTH: 28
<212> TYPE: DNA
<213> ORGANISM: Artificial Sequence
<220> FEATURE:
<221> NAME/KEY: misc_feature
<222> LOCATION: (1)...(28)
<223> OTHER INFORMATION: primer

<400> SEQUENCE: 5
gcaggatccg gtaatggtag tagtcaaa                                              28

<210> SEQ ID NO 6
<211> LENGTH: 27
<212> TYPE: DNA
<213> ORGANISM: Artificial Sequence
<220> FEATURE:
<221> NAME/KEY: misc_feature
<222> LOCATION: (1)...(27)
<223> OTHER INFORMATION: primer

<400> SEQUENCE: 6
gtagctcgag tagaatggtg gattagc                                               27
```